US005935575A

United States Patent [19]
Lenardo et al.

[11] Patent Number: 5,935,575
[45] Date of Patent: Aug. 10, 1999

[54] INTERLEUKIN-4 STIMULATED T LYMPHOCYTE CELL DEATH FOR THE TREATMENT OF ALLERGIC DISORDERS

[75] Inventors: Michael J. Lenardo, Potomac, Md.; Stefen A. Boehme, McClean, Va.; Jeffrey Critchfield, Bethesda, Md.

[73] Assignee: The United States of America as represented by the Department of Health and Human Services, Washington, D.C.

[21] Appl. No.: 08/348,286

[22] Filed: Nov. 30, 1994

Related U.S. Application Data

[63] Continuation of application No. 07/926,290, Aug. 10, 1992, abandoned.

[51] Int. Cl.$^6$ .......................... A61K 39/35; A61K 38/20
[52] U.S. Cl. .................. 424/184.1; 424/852; 424/275.1; 424/278.1; 530/868
[58] Field of Search ............................ 424/275.1, 278.1, 424/85.2, 184.1; 530/868

[56] References Cited

U.S. PATENT DOCUMENTS 4,904,481  2/1990  Fathman et al. ...................... 424/154.1

OTHER PUBLICATIONS

Van Reijsen et al, Clin. Exp. Immunology, 98: 151–157, 1994.
Romaghani et al, Int Arch Allergy Immunol, 98:279–285, 1992.
Walker et al, Am Rev. Respir Dis, 146(1): 109–115, 1992.
Lipsky et al. Scand J. Rheumatol Suppl 76:229–235, 1988.
Ghadirian et al, Microbial Pathogenesis 12:377–382, 1992.
Sambharu S.R et al, Science 252: 1424–1427, 1991.
Paul, W.E. et al, Ann. REv. Immunol S: 424–59, 1987.
Lotze MT et al, J. of Immunology 135(4):2865–2875, 1985.
Marx, J. Science 252 :27–28, 1991.
Foxwell BMJ, et al, Eur. J. Immunol 19: 1637–1641, 1989.
Lenardo MJ et al, Nature 353: 858–861, 1991.
Roitt IM et al. In *Immunology*: Gower Medical Publishing 1985 p. 24.3.
Roitt IM, In *Essential Immunology*; Blackwell Scientific Publications 1988 p. 197.
Ucker et al (1992) *The Journal of Immunology*, vol. 149, pp. 1583–1592.
Zacharchuk et al (1990) *The Journal of Immunology*, vol. 145, pp. 4037–4045.
Iseki et al (1991) *The Journal of Immunology*, vol. 147, pp. 4286–4292.
Grabstein et al (1987) *The journal of Immunology*, vol. 139, pp. 1148–1153.
Iwata et al (1991) *Eur. J. Immunol*, vol 21, pp. 643–648.
Lenardo, M.J., (1991) *Nature*, vol. 353, pp. 858–861.
Widmer et al (1987) Nature, vol. 326, pp. 795–798.
Mueller et al, "*Clonal Anergy Blocks The Response To IL–4, As Well As The Production of IL–2, In Dual–Producing T Helper Cell Clones*", citation unavailable.
Boehme et al, "Antigen Receptor–Induced Apoptosis of Nontransformed, Mature T Lumphocytes (Propriocidal Regulation), but not Glucocorticoid–Induced Apoptosis, Requires a Distinct Stage of the Cell Cycle", manuscript submitted.

*Primary Examiner*—James C. Housel
*Assistant Examiner*—Julie Krsek-Staples
*Attorney, Agent, or Firm*—Townsend and Townsend and Crew LLP

[57] ABSTRACT

This invention discloses a method for the treatment or prevention of autoimmune diseases, allergic or atopic disorders and graft rejection. Specifically, it provides a means of killing a specific sub-population of T lymphocytes while leaving the majority of other T lymphocytes in the population unaffected. The sub-population of T lymphocytes are killed by repeatedly challenging the population with an antigen in conjunction with administration of interleukin-4.

17 Claims, 2 Drawing Sheets

INTERLEUKIN-4 STIMULATED T LYMPHOCYTE CELL DEATH FOR THE TREATMENT OF ALLERGIC DISORDERS

This is a Continuation of application Ser. No. 07/926,290, filed Aug. 10, 1992, now abandoned.

BACKGROUND OF THE INVENTION

1. Field of the Invention

The present invention relates to the treatment and prevention of diseases that are primarily due to T cell immune responses. In particular, it relates to the suppression or elimination of certain autoimmune diseases, graft rejection, and allergic disorders by treatment with interleukin-4 (IL-4) and the specific antigen involved, thus allowing the killing of only the subpopulation of T cells that recognizes this specific antigen. In this manner, IL-4 pretreatment sensitizes T cells to undergo programmed cell death following T cell receptor engagement.

2. Description of Related Art

Apoptosis is a form of programmed cell death that occurs in many biological systems (1–5). An apoptotic cell undergoes a specific program of events dependent upon active metabolism that contributes to its own self-destruction. Distinct morphological changes occur during this process such as membrane blebbing and cytoplasmic and nuclear condensation. These changes are accompanied by fragmentation of genomic DNA into pieces constituting one to several nucleosomes. In the final stages, the cell disintegrates into apoptotic bodies that are specifically recognized and phagocytozed by neighboring cells.

T lymphocytes are sensitive to apoptotic cell death induced by a variety of stimuli at multiple points in their lifespan. Experimental evidence strongly suggests that programmed cell death normally plays a large role in shaping and maintaining the T cell repertoire. Repertoire here is defined by the number of distinct antigen receptor specificities contained in the entire pool of T lymphocytes in the organism. Each T lymphocyte bears surface receptors for antigen that are all of identical structure on that cell and therefore are said to represent a single antigen specificity. Since each T cell has a unique specificity, the total collection of antigen specificities in an organism is the sum of different individual T cells, thus the T cell repertoire. By eliminating or expanding the number of individual T cells, the responsiveness of an organism to a particular antigen can be either curtailed or enhanced, respectively. These changes have been documented to occur and are known as changes in the T cell repertoire. Alterations in the T cell repertoire occur naturally during T cell development such that only a small fraction of thymocytes (or immature T cells) survive the intrathymic development and selection events that allow emigration of developing T cells to the peripheral circulation (6,7). The majority of thymocytes appear to undergo apoptotic cell death in the thymus because they bear particular receptors. This "editing" of the T cell repertoire is thought to be the result of two processes: lack of positive selection, and negative selection or clonal deletion. The latter is fundamental to the establishment of self-tolerance as cells expressing potentially autoreactive receptors are actively eliminated. Fetal thymic organ culture (8), in vivo (9), and in vitro (10,11) experiments have shown that the double positive ($CD4^+, CD8^+$) thymocytes appear to be more sensitive to apoptotic death induced by T cell receptor occupancy than more mature single positive cells. These double positive cells are also sensitive to programmed cell death induced by glucocorticoids (12).

Transformed T cells undergo activation-induced death from stimuli that are normally mitogenic for T cells (13–19). These include antigen, anti-TCR or CD3 mAb binding, the combination of phorbol ester and $Ca^{2+}$ ionophore, and mAb modulation of alternative activation molecules Thy-1 and Ly-6. These cells are also susceptible to glucocorticoid-induced apoptosis. The processes of activation- and glucocorticoid-induced programmed cell death are mutually antagonistic in transformed T cells (20–22).

Mature untransformed T cells have been shown to undergo apoptosis in response to various stimuli, such as IL-2 deprivation in the case of cells requiring IL-2 for viability (23), and modulation of the Fas antigen by the APO-1 mAb (24,25). Additionally, it has recently been demonstrated that IL-2 programs mature T lymphocytes to undergo apoptosis in response to antigen receptor stimulation both in vitro and in vivo (26). T cells must be under the influence of IL-2 prior to T cell receptor stimulation for apoptosis to occur, and the amount of cell death rises with increased amounts of IL-2. This process is selective, such that only stimulated T cells triggered by their specific antigen receptor and not by bystander cells undergo cell death. This apparent feedback pathway, termed propriocidal regulation, may represent a mechanism by which T cell responses are regulated (26).

The discovery that interleukin-4 (IL-4) predisposes T lymphocytes to programmed cell death, or apoptosis, allows for a novel method of therapeutic intervention in disease processes in humans and animals primarily caused by the action of IL-4-responsive T cells (27). In essence, this involves specifically inducing the death of a subpopulation of T lymphocytes that are capable of causing disease, while leaving the majority of T lymphocytes substantially unaffected. This method of intervention contrasts with, and is potentially far superior to, currently used therapeutic methods that cause a general suppression or death of T lymphocytes. Examples of widely-used general immunosuppressive agents are corticosteroids, such as prednisone, which are used to treat autoimmune diseases and allergic conditions, and cyclosporin A, which is used for treating graft rejection (28). These treatments suffer from the drawback of severely compromising immune defenses, by debilitating a large portion, if not the entire T cell repertoire. This leaves the patient vulnerable to infectious diseases. The two key elements of the present process are that: i) only the subset of T cells that reacts with antigens that cause the disease are affected by the treatment; and ii) the T cells affected by the treatment are killed, i.e., they are permanently removed from the repertoire.

Several general principles underlie the present process. T cells recognize antigen in the form of short peptides that form noncovalent complexes with major histocompatibility complex (MHC) proteins on the surface of antigen-presenting cells found throughout the body (29). Antigens may also take the form of polysaccharides, organic molecules, or nucleic acids. Each T cell bears a unique antigen receptor called the T cell receptor (TCR) that is capable of recognizing a specific antigen-MHC complex. Through rearrangement of the gene segments containing the protein-coding segments of the TCR, a vast array, perhaps a virtually unlimited number of combinations, of different TCRs are generated (30). By a mechanism termed "allelic exclusion", each T cell bears a single unique TCR. The T cell repertoire is therefore a large number of T cells, each with a distinct TCR that recognizes a specific antigen-MHC complex. It is this vast array of T cells that allows immunological responses to the diversity of antigenic structures on invading micro-organisms, tumor cells, and allografts, thus preserving the integrity of the organism.

Most antigens are able to elicit a response in only a very tiny fraction of the T cell repertoire (31). For example, the initial response to protein antigens may involve as few as 1 in 1000 to 1 in 10,000 T lymphocytes (32). For this reason, diseases caused by T cell reactivity are mediated by only a small subset of the large repertoire of T cells (33). In particular, in those cases where it has been directly measured, such as in multiple sclerosis, the fraction of the T cell repertoire which mediates disease is quite small (33). The important feature of the T cell subset that participates in disease is that it involves T cells which specifically recognize an antigen that provokes the disease. In allergic conditions, the antigen causes the release of inflammatory response molecules. For example, "helper" T cells secrete lymphokines such as IL-4 that cause B cells to produce the inflammatory antibody IgE. In autoimmune diseases, the antigen may be derived from a specific organ in the body and, when recognized by a subset of T cells, stimulates the T cells to attack that organ. A similar effect occurs during graft rejection. Antigenic proteins in the transplanted organ evoke a response in a subset of T cells that attacks the engrafted tissue. For unknown reasons, the fraction of T cells recognizing foreign or "allo" tissue is significantly higher than the number that will typically recognize a protein antigen. Nonetheless, the number of responding T cells is still a distinct minority (1–10%) of the overall T cell repertoire (34).

In a typical T cell response to a specific antigen-MHC complex, stimulation of the TCR (35) results in a cascade of gene activation events. These have been extensively characterized at the molecular level, and two such activation events are especially germane to the present invention i) production of growth lymphokines such as IL-4 and ii) expression of the cell surface proteins that constitute high-affinity receptors for IL-4. Resting T cells express small numbers of high affinity IL-4 receptors; this number increases following activation (36). IL-4 is a 15,000 dalton protein that causes T cells bearing the appropriate high affinity receptor to divide (37,38). The production of IL-4 followed by its interaction with its receptor causes an autocrine mechanism that drives the T cells into the cell cycle. This leads to an initial expansion of T cells that are specifically reactive with the antigen. At present, evidence indicates that in both the human and murine immune systems, a subclass of T lymphocytes called CD4$^+$ T$_H$2 cells may proliferate after antigen activation by producing and responding to IL-4 (39). This subset plays an important and perhaps unique role in stimulating B cells to produce immunoglobulin (Ig) (40). This is because IL-4 and other lymphokines produced by T$_H$2 cells, such as IL-5 and L-6, act as differentiation factors for B cells that are crucial for Ig production. Therefore, in autoimmune diseases in which Ig plays a pathogenetic role, the elimination of CD4$^+$ T$_H$2 lymphocytes represents a highly effective way to halt disease. Our results and those of others (27,40–43) show that other classes of T cells including CD4$^+$ T$_H$1 type lymphocytes that mediate delayed-type hypersensitivity as well as CD8$^+$ cells that mediate cytotoxicity will also proliferate in response to IL-4 and are predisposed to TCR induced apoptosis. Therefore, IL-4 has a potentially broad role in T cell growth during immune responses. Thus, IL-4 could be broadly active in different classes of T cells to predispose them to apoptosis. The present inventive discovery indicates that IL-4 also has the surprising effect of predisposing the expanded pool of either human or mouse T cells to apoptosis or programmed cell death if they are again stimulated or rechallenged through the TCR (27). In the present work described supra, the degree of apoptosis achieved in T cells is correlated positively with both the level of IL-4 the cells experience during their initial expansion, the strength of the TCR stimulation upon rechallenge, and the timing of the rechallenge. In lymphokine-predisposed apoptosis, the effects wear off 2–3 days after lymphokine is no longer present, hence rechallenge must occur within that period (44). The process of activation and apoptosis eventually depletes the antigen-reactive subset of the T cell repertoire.

Apoptosis is a type of programmed cell death in which the T cell nucleus shrinks, the genetic material (DNA) progressively degrades, and the cell collapses (1–5). Evidence suggests that cells cannot recover from apoptosis, and that it results in irreversible killing (1–5). T cells that do not undergo apoptosis but which have become activated will carry out their "effector" functions by causing cytolysis, or by secreting lymphokines that cause B cell responses or other immune effects (45). These "effector" functions are the cause of tissue damage in autoimmune and allergic diseases or graft rejection. A powerful approach to avoiding disease would therefore be to permanently eliminate by apoptosis only those T cells reactive with the disease-inciting antigens, while leaving the majority of the T cell repertoire intact. Apoptosis and T cell deletion caused by antigenic stimulation have been demonstrated in model systems, but since a mechanism for this phenomenon was not previously known, it was not possible to use this in a therapeutically effective way (46–50).

By using IL-4 as an agent that predisposes T cells to death by TCR stimulation in appropriate cycle with immunization with the antigen(s) leading to autoimmune disease or graft rejection, the death of disease-causing T cells can be invoked. Specific methods are described for i) treatment of autoimmune or allergic diseases by identified protein antigen and IL-4, and ii) treatment of graft rejection by blood cell antigens and IL-4. Such methods, by logical extension, can be further developed for other diseases of man or animals that result from the effects of T cells activated by specific antigens. Because the vast majority of immune responses depend on T cell activation, it is predicted that this form of therapy could be applied to a wide variety of autoimmune and allergic conditions especially where antibody production is involved (51,52).

In several human autoimmune diseases, data have indicated that antigen-activated T cells play a key role in the production of disease. These include but are not limited to: 1) multiple sclerosis (53–58); 2) uveitis (59,60); 3) arthritis (61–63); 4) Type I (insulin-dependent) diabetes (64,65); 5) Hashimoto's and Grave's thyroiditis (66–68); and 6) autoimmune myocartiditis (69). The ethical limits on human experimentation have made it very difficult to prove that T reactivity is the sole inciting agent of these diseases. Nonetheless, a large body of experimental work on animal models—murine experimental allergic encephalitis as a model for multiple sclerosis (70,71), BB diabetic rats for human diabetes (72,73), murine collagen-induced arthritis for rheumatoid arthritis (74,75), and S antigen disease in rats and guinea pigs for human autoimmune uveitis (76, 77), among others—suggests that T cells are the critical agent of these diseases. From recent work, the identity of disease-causing proteins or peptide antigens is emerging: i) multiple sclerosis: the peptide epitopes of myelin basic protein (MBP) residues 84–102 and 143–168 (54,57,78,79); ii) autoimmune uveitis: the human S antigen, which has been recently molecularly cloned (59, 80); iii) type II collagen in rheumatoid arthritis (81); and iv) thyroglobulin in thyroiditis (82). Similarly, a wide variety of proteins have been identified which stimulate the production of the allergic immunoglobulin IgE, which is the underlying immunological reaction for common allergies. IgE is produced by B lymphocytes in a process that requires lymphokines produced by antigen-activated T cells known as "T cell help". The class of $CD4^+$ "helper" T cells that stimulate B cells ($T_H2$ cells) typically produce and respond to IL-4 (39,40).

The basic concept of the present therapeutic approach is very simple. Disease-causing T cells are first challenged by immunization to cause the activated T cells to express high affinity IL-4 receptors and, for $T_H2$ cells, to begin producing and secreting IL-4. When the cells are expressing high levels of IL-4 receptor, additional human IL-4 is infused to very efficiently drive all the activated cells into the cell cycle. The cells under the influence of IL-4 are then caused to undergo apoptosis by re-immunization with antigenic peptide or protein. Further, if the antigen is capable of stimulating sufficient IL-4 production, it may not be necessary to administer exogenous IL-4. In either case, the timing of rechallenge is important—it must occur within a short interval such as 2–3 days after the first stimulus when cells bear high levels of the IL-4 receptor and are responding to exogenous or endogenous IL-4.

The conceptual advance provided by the inventive discovery that underlies the present methods is that T cell immunity works as a balance between the production and destruction of antigen-specific T lymphocytes. Previously, investigators have focused on the use of lymphokine growth factors such as IL-4 to increase the proliferation and responsiveness of T lymphocytes (38,43,83–87). It is now proposed that the opposing T cell mechanisms be used therapeutically. The discovery that IL-4 predisposes T cells to death is contrary to the previously understood properties of IL-4, and provides a radically new approach to the treatment of diseases caused by T cell reactivity. By providing physicians and medical researchers with the basis of the present inventive discovery, the processes of immune autoregulation leading to T cell destruction can be exploited in combatting disease.

It has been previously known for some time that prior activation and lymphokine production were capable of diminishing immune responsiveness both in vivo and in vitro (46–48). The mechanisms underlying these effects were not understood. Absent the knowledge that IL-4 predisposes T lymphocytes to antigen-dependent apoptosis, it was not possible to manipulate this phenomenon for medical or therapeutic purposes. It is now possible to rigorously study the kinetics and dose requirements of IL-4 in the predisposition phase, and antigen in the apoptosis phase, to routinely optimize the treatment cycle for a given disease following the guidance provided herein.

That this process depends on the discovery of a novel property of IL-4 is particularly auspicious. IL-4 has been thoroughly studied since its discovery in 1982 (85,86). It is well-understood genetically, its cDNA and gene have been molecularly cloned, and antibodies against the protein for immunodetection have been prepared (87,88). IL-4 is already available pharmaceutically in a form for use in humans and studies in human cancer victims have given insights into how IL-4 affects human physiology at different doses (89–92). All of these features significantly enhance the feasibility of its novel use to cause auto-destruction of disease-causing T lymphocytes for the treatment of a wide variety of diseases in humans and other mammals.

SUMMARY OF THE INVENTION

The present invention arose from the discovery that IL-4 programs mature T cells for antigen-driven death. The T cell death caused by IL-4 followed by antigen stimulation has hallmarks, such as DNA fragmentation, of "programmed cell death" or apoptosis. Thus, IL-4 acts as a death cytokine that triggers the demise only of T cells that are specifically stimulated through their antigen receptor. This invention therefore allows the capability of altering the T cell repertoire much the same way that negative selection in the thymus naturally eliminates T cells having certain antigen specificities. This novel use of a previously undiscovered property of IL-4 will allow the specific elimination of certain classes of antigen receptor-bearing T cells, forming the basis for new clinical applications of IL-4.

IL-4 is a lymphokine produced by T lymphocytes that was originally discovered to cause the growth of B lymphocytes (85). Later it as found that this molecule had pleiotropic activities on B cells such as increasing surface expression of MHC class II molecules, elevating immunoglobulin secretion and class switching and inducing the presence of Fcε receptors. (93) Most importantly, IL-4 had powerful effects on both $CD4^+$ and $CD8^+$ T cells (37–43). IL-4 strongly enhanced the activity of cytolytic T cells which are involved in graft rejection (42). Also, IL-4 is a potent T cell growth factor. (37,38,43) Among helper T lymphocytes, IL-4 promotes the growth of $T_H2$ cells that produce IL-4 in response to antigen stimulation and help B cells mount an antibody response (40).

A critical determinant of the choice between T lymphocyte proliferation or programmed cell death is the prior exposure of these cells to IL-4. Antigen receptor stimulation in T cells not exposed to IL-4 causes normal activation, leading to lymphokine production and growth. In contrast, T cells previously exposed to IL-4 undergo apoptosis after antigen receptor stimulation. Therefore, antigen-activated T cells that are under the immediate influence of IL-4 will respond to rechallenge by antigen by undergoing apoptosis. The timing is significant because later antigenic stimulation can cause growth rather than apoptosis if the cells are no longer under the influence of IL-4 if, for example, IL-4 is removed and the T cells are allowed to return to their resting state.

At least three uses for this novel property of IL-4 can be envisioned.

First, there is an emerging set of findings that show that infusion of peptides derived from antigens involved in autoimmune diseases leads to the lessening of severity of such diseases (cf. 94). A variety of studies of the autoimmune disease experimental allergic encephalitis (EAE) shows that it is caused by the activation of T cells by immunization with myelin basic protein (MBP). Interestingly, infusion of peptides derived from the MBP sequence that stimulate the T cells that generate the disease are effective at blocking the disease (71). The discovery disclosed herein provides an explanation for these seemingly paradoxical observations, which is that the T cells are activated and are potentially stimulated by IL-4 during peptide infusion, and then undergo apoptosis when they are restimulated by the MBP antigen. Human diseases that have been associated with T cell activation by peptide antigens include multiple sclerosis and autoimmune uveitis (78,80). It is envisioned that these diseases, and, for example, systemic lupus erythematosus, systemic vasculitis, polymyositis-dermatomyositis, systemic sclerosis (scleroderma), Sjogren's Syndrome, ankylosing spondylitis and related spondyloarthropathies, rheumatic fever, hypersensitivity pneumonitis, allergic bronchopulmonary aspergillosis, inorganic dust pneumoconioses, sarcoidosis, autoimmune hemolytic anemia, immunological platelet disorders, cryopathies such as cryofibrinogenemia, autoimmune polyendocrinopathies, and myasthenia gravis can be approached by therapy which can now be potentially modulated in a rationale way using IL-4 and the relevant peptide to cause apoptosis of the T cells responsible for the disease. Not all T cells have a propensity to produce and respond to IL-4. However, the $T_H2$ class of T lymphocytes which produce and respond to IL-4 are crucial as "helper" cells for immunological responses that involve the production of antibody. Many of the autoimmune diseases mentioned above have an antibody component that leads directly to pathology (as in myasthenia gravis) or indirectly to pathology by immune complexes (as in systemic lupus) (51). Therefore, the elimination of $T_H2$ "helper" cells may provide a significant amelioration or cure of these diseases. By targeting a population of T cells that respond to IL-4 for apoptosis, this invention significantly extends a previous discovery that IL-2 predisposes T cells to apoptosis (26). The appropriate time of IL-4 infusion or a repetitive immunization schedule could substantially augment the protective effect of the infused peptides.

Secondly, there is a significant body of literature that suggests that pre-immunization of an animal or man prior to engraftment with a foreign tissue prolongs the survival time of the graft (cf. 95). One example of this phenomenon is the "donor-transfusion effect," in which transfusing a patient about to receive an organ transplant with blood from the organ donor decreases rejection of the transplant. Studies have shown that $CD8^+$ cells will grow in response to IL-4 (42,43) thereby potentially rendering $CD8^+$ cells susceptible to IL-4-mediated apoptosis. This is the primary class of T cells involved in graft rejection. Based on the discovery of this novel property of IL-4, $CD8^+$ T cells may be induced to undergo IL-4-mediated apoptosis; administering IL-4 during and immediately after the preimmunization/transfusion phase, or repetitive immunization with MHC antigen at appropriately short intervals, could augment T cell death, leading to greater tolerance of grafts.

Thirdly, a wide variety of atopic or allergic disorders, commonly known as asthma or allergies, results from the effects of activating T cells, which causes both the release of harmful lymphokines and the production of IgE by B cells (96,97,98). Over the past few decades, clinicians have made primitive attempts to treat these diseases by a "desensitization" process consisting of repetitive exposure to the same antigen that elicited the allergy (97). Despite the fact that very little is known about the mechanisms set in play by this procedure, in some cases such treatments were highly successful (97). An important scientific by-product of this work in clinical allergy is that considerable effort has gone into identifying proteins and other molecules that cause allergic responses (98). This has led to the identification of protein sequences for antigens such as Amb a V and Amb t V, which are ragweed allergens that cause hay fever, the protein sequence and characterization of antigenic peptides from allergen M that causes allergy to codfish (99), and the molecular cloning of the cDNA for antigen 5 of white-face hornet venom, associated with allergy to hornet stings (100). Drugs that can cause allergy are typically small organic molecules that may become immunogenic by forming covalent complexes with host proteins. In addition, a large variety of allergens have been prepared as protein extracts to be administered clinically to humans under the supervision of the Food and Drug Administration, and evaluated by a Panel on Review of Allergenic Extracts (97). With the molecular identification of these and other allergy-evoking antigens, it will be possible to immunize in cycle with IL-4 (See page 12 and FIG. 3) to induce apoptosis of T cells involved in allergic disorders such as allergic rhinitis, bronchial asthma, anaphylactic syndrome, urticaria, angioedema, atopic dermatitis, allergic contact dermatitis, erythema nodosum, erythema multiforme, Stevens-Johnson Syndrome, cutaneous necrotizing venulitis, and bullous skin diseases.

Because a key component of the allergic response is the production IgE antibody that depends on "helper" T cells that respond to IL-4 (96), it is likely that IL-4 mediated apoptosis of T cells could have a significant effect on allergic disease processes.

The key feature of each of these treatment protocols is that only the antigen-specific T cells, which comprise only a small component of the patient's T cell repertoire, would be eliminated. The treatment would leave the patient's immune system largely intact. This is in contrast to present treatments that rely upon general immunosuppression that seriously incapacitates the host's immune function (see 101). Moreover, because this treatment causes death of the T lymphocytes, it is superior to other recently discovered mechanisms which do not kill T cells but rather cause functional inactivation or anergy that is typically reversible (102–104). The experimental results described infra therefore have broad clinical significance in applications to human immunological diseases.

Throughout the history of immunological approaches to human and animal diseases, beginning with the first vaccination against smallpox carried out by Edward Jenner in 1798, the emphasis has been on stimulating a positive and protective antigen-specific immune response. In modern immunology, this is known to be due to activating lymphocytes. Hence, causing the activation and proliferation of antigen-specific immune cells, especially T lymphocytes, forms the basis of most of the clinical applications of immunology. In particular, the recent advent of molecularly cloned cytokines, especially those with the ability to cause the proliferation of immune cells, has furthered the clinical application of immunology. Such molecularly cloned cytokines can be readily prepared pharmacologically, and are powerful agents for stimulating the growth and division of lymphocytes. The conceptual and practical advance offered by the discovery disclosed herein is that cytokines such as IL-4, when given in sufficient quantity, also cause negative regulatory effects such as T cell apoptosis. These regulatory effects represent built-in mechanisms to limit or suppress the immune response. Thus, the recognition that these mechanisms exist, and the identification of a biologic, IL-4, that potently evokes antigen-specific T cell death, offers the opportunity to exploit the negative regulation of the immune response for the treatment of disease.

Accordingly, it is an object of the present invention to provide a method for treating or preventing disease in a human or animal caused by antigen-activated T cells. This method induces the death by apoptosis of a subpopulation of T lymphocytes that is capable of causing said disease to an extent greater than that of other T lymphocytes. Said disease can include an autoimmune disease, graft rejection, or an allergic or atopic disorder, and said apoptosis can be achieved either by exploiting endogenous IL-4, or by administering this substance exogenously. When IL-4 is administered exogenously, apoptosis can be achieved by a cycle comprised of challenging specific T cells via immunization with a substance selected from the group consisting of an antigen, a peptide, a protein, a polysaccharide, an organic molecule, and a nucleic acid, followed by administering a high dose of IL-4 when said T cells are expressing high levels of IL-4 receptor, so as to cause said T cells to undergo apoptosis upon reimmunization with said substance. When endogenous IL-4 is employed to achieve apoptosis, said cycle comprises challenging said T cells via immunization by repeated administration of said substance at intervals appropriate to cause apoptosis without the subsequent administration of a high dose of IL-4, relying instead on endogenous levels of IL-4.

Further scope of the applicability of the present invention will become apparent from the detailed description and drawings provided below. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which:

FIG. 1. Photomicrographs of IL-4 treated A.E7 cells in the presence or absence of T cell receptor stimulation. IL-4 responsive A.E7 cells were cultured in medium alone or with platebound anti-CD3ε mAb (145-2C11) for 48 hours. For photomicroscopy, the medium was replaced with 0.4% trypan blue in phosphate buffered saline (PBS, 0.8 M potassium phosphate, 154 mM sodium chloride, and 2.9 mM sodium phosphate, pH 7.4). The trypan blue stain was removed and the wells were gently washed three times with PBS only. Photomicrographs were made on a Zeiss Axiovert 405 M microscope using Hoffman modulation contrast optics.

DETAILED DESCRIPTION OF THE INVENTION

The following detailed description of the invention is provided to aid those skilled in the art in practicing the same. Even so, the following detailed description should not be construed to unduly limit the present invention, as modifications and variations in the embodiments herein discussed may be made by those of ordinary skill in the art without departing from the spirit or scope of the present inventive discovery.

The disclosures of each of the references cited in the present application are herein incorporated by reference in their entirety.

MATERIALS AND GENERAL METHODS

Materials. Female B10.A and BALB/c mice were purchased from Charles River. Pigeon cytochrome c, and propidium iodide, as purchased from Sigma Chemical Co. (St. Louis, Mo.). Purified murine rIL-4 was kindly provided by Dr. W. Paul (National Institute of Allergy and Infectious Diseases, NIH). The anti-murine IL-2 monoclonal antibody (mAb) S4B6.1 was generously provided by Dr. J. Zùniga-Pfl ücker (National Institute of Allergy and Infectious Diseases, NIH). Anti-murine CD3ε mAb 145-2C11 (105) used in experiments was immobilized by coating either 12- or 96-well culture plates (500 $\mu$l or 100 $\mu$l, respectively) (Costar, Cambridge Mass.), at a concentration of either 1 $\mu$g/ml or 10 $\mu$g/ml in phosphate-buffered saline (PBS) for 120 minutes or overnight at 37° C. The plates were washed three times with medium (Click's or Eagle's Hank's amino acid, EHAA, and 10% FCS, 2 mM glutamine, 50 $\mu$M β-mercaptoethanol, penicillin and streptomycin; Biofluids, Inc., Rockville, Md.) before use. mAbs specific for MHC class II molecules ($A^k$, 10.2.16; and $E^k$, Y17), were a gift from Dr. R. Schwartz (National Institute of Allergy and Infectious Diseases, NIH).

Cell culture. The murine nontransformed T cell clone A.E7 was carried as described previously (106). For experimentation, either resting cells (>2 weeks following antigen stimulation) or antigen stimulated cells were used. Antigen stimulation consisted of culturing $1\times10^6$ resting T cells with $1\times10^7$ B10.A irradiated (3000R) splenocytes and 5 $\mu$M pigeon cytochrome c in 2 mls total volume. After 48 hours, the antigen presenting cells (APCs) were removed by MHC class II mAb mediated complement lysis (low-tox-M rabbit complement, Cedarlane Laboratories, Westbury, N.Y.), and the cells were recovered by Lympholyte M density centrifugation (Cedar Lane Laboratories) as previously described (41,104). The cells were then recultured for 48 hours in medium with 1% MLA (gibbon ape leukemia cell supernatant containing 140 U/ml of IL-2 activity) or rIL-4 (10–1000 U/ml). T cells were then harvested and washed and assays were carried out in 96-well flat-bottomed plates in triplicate, with 200 $\mu$l total volume for 48 hours. $5\times10^4$ cells/well (with the exception of Table I, Experiment 1 which was $1\times10^5$ cells/well) were added with the designated lymphokine, either in the absence or presence of T cell receptor stimuli. The live cell number was then determined as described below.

T cell proliferation assays. A parallel culture of $5\times10^4$ cells, without T cell receptor (TCR) stimulation, was pulsed by the addition of 1 $\mu$Ci of [$^3$H] thymidine ($^3$H-TdR) (6.7 $\mu$Ci/mmol, New England Nuclear) for 16–24 hours. Cells were subsequently harvested onto glass filter paper, and the samples counted by liquid scintillation on an LKB betaplate counter. Data are expressed as the mean cpm of triplicates.

Cell viability. Viable cell number was determined by manual counting of trypan blue excluding cells using a hemocytometer by flow cytometry (FACS) with propidium iodide stained cells. For flow cytometry quantitation, cells were harvested by pipetting, washed once in phosphate buffered saline (PBS), and each sample was suspended in a constant volume of PBS with propidium iodide (2 $\mu$g/ml). The fluorescence intensity of samples collected for a constant amount of time (100 sec.) was determined using a FACSCAN II analyzer with Lysis II software (Becton Dickenson, Mountain View, Calif.).

For this procedure, each sample is kept in a constant volume and the cells are collected for a constant amount of time, independent of the number of events. Only the live cell number, as gated by forward scatter and propidium iodide exclusion, is quantitated. A comparison between duplicate cultures analyzed for live cell number by trypan blue exclusion or flow cytometric analysis reveals that the relationship between these two quantitation methods is linear, evidenced by an R value >0.97.

Analysis of DNA Fragmentation in Agarose Gels.

$1 \times 10^6$ cells were incubated in 12-well plates coated with anti-CD3ε mAb for 48 hours, at which time the cells were harvested by gentle scraping and prepared by a modification of a previous procedure (8). Briefly, cells were washed once in PBS and incubated in 20 μl of lysis buffer (50 mM Tris, pH 8.0, 10 mM EDTA, 500 μg/ml proteinase K, and 0.5% sodium sarkosyl) for 1 hour at 50° C. RNase A (50 μg/ml) (Boehringer Mannheim) was added and the cells were incubated for an additional hour at 50° C. Dye buffer (10 mM EDTA, 1% (w/v) low melting point agarose, 0.25% (w/v) bromphenol blue, and 40% (w/v) sucrose) was added, the samples were heated to 70° C. for five minutes, quenched on ice, and electrophoresed in a 2% Nusieve agarose, 1% ultra-pure agarose gel with ethidium bromide.

EXAMPLE I

IL-4 Predisposes T Cells to Antigen-Induced Apoptosis.

We have previously shown that IL-2 participates in an apparent feedback pathway, termed propriocidal regulation, by predisposing T lymphocytes to antigen-induced apoptosis (26). We therefore determined if IL-4, another T cell growth factor, would induce this pathway. We first studied the nontransformed CD4$^+$ T$_H$1 clone A.E7 that responds to pigeon cytochrome c in the context of an E$^k$ MHC class II molecule. This clone has been shown to upregulate its IL-4 receptor in response to antigenic stimulation and proliferate in response to IL-4 (41). As shown in Table 1, antigen stimulated A.E7 cells proliferate to IL-4 in a dose dependent manner, as indicated by tritiated thymidine ($^3$H-TdR) incorporation (experiment 1). Moreover, there was a dramatic cell loss when the proliferating cells were subsequently placed onto anti-CD3ε-coated plates for 48 hours, as compared to the uncoated plate control. The reduction in cell number was minimal with no growth lymphokine added and increased roughly in proportion to the degree of proliferation achieved with increasing amounts of lymphokine. Cells treated with 1000 U/ml IL-4 showed an 84% decrease in cell number following TCR stimulation. The overall cell loss found with IL-4 was as great as that obtained with IL-2 stimulation (85% versus 87%, respectively).

We observed a similar phenomenon with the lymphokine-dependent T cell lines, CR.4R and CT.4S. We could not detect any T cell receptor surface expression in either cell line and anti-CD3ε stimulation had no effect on these cells (S.B. and M.L., unpublished results). Nonetheless, when TCR occupancy was mimicked by a combination of phorbol myristic acetate (PMA) and ionomycin, extensive cell loss was observed after 48 hours (Table 1, experiment 2). Greater than 90% cell loss was observed for CT.4R cells exposed to either IL-2 or IL4, and 87% cell loss was seen for CT.4S cells incubated with IL-4.

Figure 1A:
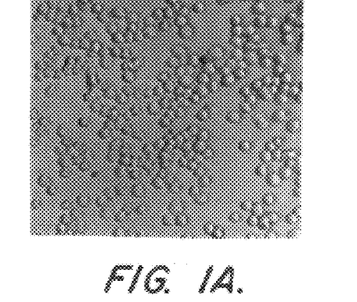
Figure 1B:
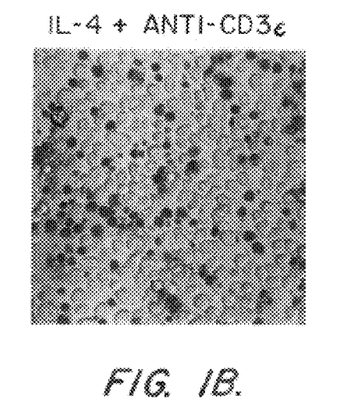
Figure 2:
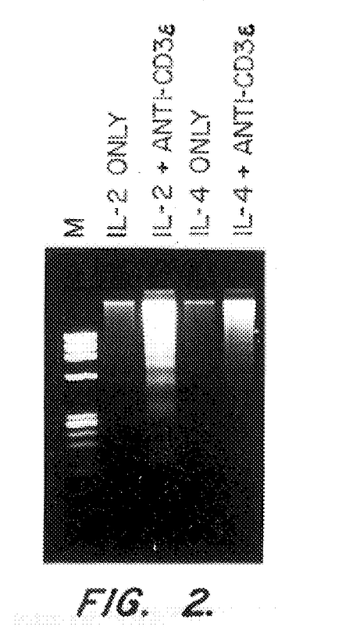
FIG. 2. A.E7 cells treated with IL-2 (14 U/ml) or IL-4 (1000 U/ml) undergo apoptosis when cultured with anti-CD3ε mAb (145-2C11). Analysis of DNA integrity by agarose gel electrophoresis of IL-2 stimulated (lanes 1 and 3), and IL-4 stimulated (lanes 2 and 4) A.E7 cells that were cultured in medium alone (lanes 1 and 2), or with platebound anti-CD3ε mAb (lanes 3 and 4).

Several features of the cell loss in these experiments suggested that cell death was occurring. First, microscopic examination in all cases revealed cells appearing to undergo apoptosis. As shown in FIG. 1, trypan blue staining can detect non-viable cells (dark colored) in the cells stimulated with anti-CD3ε antibody more than in untreated samples. Second, the number of A.E7 cells following 1000 U/ml IL-4 and anti-CD3ε stimulation was less than the number of cells put into the wells implying cell loss in addition to any potential block in proliferation (Table 1, experiment 1). Third, ladders of nucleosomal length DNA were obtained following IL-4 and anti-CD3ε treatment of A.E7 cells, indicating the occurrence of apoptosis. As shown in FIG. 2, DNA fragmentation was observed in cells cultured with platebound anti-CD3ε mAb (lanes 3 and 4), and was not observed in cells cultured with medium alone (lanes 1 and 2). We also observed cell death when IL-4 treated A.E7 cells were co-cultured with irradiated splenocytes and antigen (Table 1, experiment 3). Because IL-4 can stimulate the release of IL-2 under certain conditions (107), a mAb capable of binding IL-2 (S4B6.1) was included in the IL-4 stimulation. This did not inhibit subsequent T cell stimulation-induced apoptosis (Table 1, experiment 4), suggesting IL-4 treatment alone predisposes T cells to apoptosis.

Because these experiments were carried out in T cell clones that had been carried in vitro for a long period of time, we investigated whether IL-4 could predispose lymph node cells to apoptosis. Conditions for stimulating lymph node T (LNT) cells to produce lymphokines and proliferate in response to either IL-2 or IL-4 have recently been determined (108). Treatment with TCR stimulation and IL-2 produces cultures exhibiting a predominantly TN1 phenotype producing and responding to IL-2, whereas the inclusion of IL-4 leads to a T$_H$2 phenotype of cells producing and responding to IL-4 (108). Freshly isolated lymph node cells were treated for 72 hours with either soluble anti-CD3ε mAb or concavalin A, and IL-2 or IL-4. The LNT cells proliferated significantly in response to lymphokine in all samples (Table 2, CPM). There was large decrease in the number of live cells recovered following a 48-hour incubation on anti-CD3ε-coated plates compared to the plastic control at all conditions tested (Table 2). These results show that IL-4 has the ability to predispose LNT cells to apoptosis. Furthermore, as was previously observed with IL-2 (26), IL-4 by itself can evoke the propriocidal pathway that leads to apoptosis following antigen receptor stimulation.

TABLE 1

The effect of IL-4 and T cell receptor stimulation on T cell viability.

| Exp. | Cells | Pretreatment[1] | CPM | Control | Anti-CD3 | % Cell Loss |
|---|---|---|---|---|---|---|
| | | | | Cell Number ($\times 10^{-5}$/ml) | | |
| 1 | A.E7 | None | 2,060 | 7.3 ± 0.7 | 5.4 ± 0.7 | 27 |
| | A.E7 | 14 U ml$^{-1}$ IL-2 | 173,845 | 37.3 ± 4.1 | 4.7 ± 0.4 | 87 |
| | A.E7 | 10 U ml$^{-1}$ IL-4 | 2,275 | 6.3 ± 0.3 | 4.7 ± 0.4 | 25 |
| | A.E7 | 100 U ml$^{-1}$ IL-4 | 17,833 | 10.1 ± 0.8 | 5.5 ± 0.8 | 45 |
| | A.E7 | 1000 U ml$^{-1}$ IL-4 | 89,159 | 18.6 ± 0.4 | 3.0 ± 0.4 | 84 |
| | | | | | PMA/I[2] | |
| 2 | CT.4R | 28 U ml$^{-1}$ IL-2 | 313,574 | 55.3 ± 5.4 | 2.9 ± 0.9 | 95 |
| | CT.4R | 1000 U ml$^{-1}$ IL-4 | 317,227 | 34.3 ± 4.6 | 3.6 ± 0.8 | 90 |
| | CT.4S | 1000 U ml$^{-1}$ IL-4 | 155,982 | 27.7 ± 1.8 | 3.6 ± 0.7 | 87 |
| | | | | FACS Cell Number[3] | | |
| | | | | −Ag | +Ag | |
| 3 | A.E7 | 1000 U ml$^{-1}$ IL-4 | 257,568 | 22,703 | 5,348 | 76 |
| | | | | | Anti-CD3E | |
| 4 | A.E7 | 14 U ml$^{-1}$ IL-2 | 266,137 | 11.7 ± 1.6 | 2.6 ± 0.4 | 78 |
| | A.E7 | 1000 U ml$^{-1}$ IL-4 | 257,913 | 9.4 ± 1.7 | 1.9 ± 0.3 | 80 |
| | A.E7 | 1000 U ml$^{-1}$ IL-4 + S4B6.1 | 257,568 | 9.3 ± 1.3 | 2.0 ± 0.5 | 79 |

[1]Indicates the treatment of A.E7 cells following 48 hour antigen stimulation. CT.4R and CT.4S cell lines did not undergo antigen stimulation but were pretreated as described. The concentration of lymphokine indicated was kept constant for each sample during the 48 hour pretreatment and the 48 hour duration of the experiment.
[2]These cells do not express TCR on the cell surface, so were cultured with PMA (10 ng/ml) and ionophore (2 μM).
[3]Indicates the live A.E7 cell number as determined by forward scatter profile, propidium iodide dye exclusion and surface staining with anti-mouse Vα1 mAb (Pharmingen) (see Materials and Methods). Experimental conditions consisted of a 10-fold excess of B10.A irradiated spleen cells, 1 μM pigeon cytochrome c (+Ag) and 30 μg of anti-mouse IL-2 μAb S4B6.1.

TABLE 2

The effect of lymphokines and antigen receptor stimulation on lymph node cell viability.

| Pretreatment | | | | | |
|---|---|---|---|---|---|
| TCR Stim. | Lymph-okine | CPM | Cell Number | | Cell Loss |
| | | | Control | Anti-CD3E | |
| Anti-CD3ε | IL-2 | 85,912 | 16,876 ± 3,775 | 7,917 ± 1,310 | 53 |
| Con A | IL-2 | 54,835 | 28,226 ± 660 | 8,489 ± 2,804 | 70 |
| Anti-CD3ε | IL-4 | 93,725 | 42,920 ± 3,409 | 4,628 ± 475 | 89 |
| Con A | IL-4 | 81,562 | 36,930 ± 2,705 | 3,510 ± 887 | 91 |

BALB/c lymph node cells were cultured at a concentration of $1\times10^6$ cells/ml for 72 hours with soluble anti-CD3ε (3 μg/ml) or Concavalin A (3 μg/ml) in the presence of IL-2 (14 U/ml) or IL-4 (1000 U/ml). The cells ($5\times10^4$ cells/well) were washed extensively and incubated with medium or anti-CD3-coated plates for an additional 48 hours in the presence of lymphokine. The cells were then harvested and the live cell number was determined by FACS analysis.

We previously proposed the term propriocidal regulation for the antigen receptor-stimulated apoptosis of mature T lymphocytes that were induced into the cell cycle by IL-2 (26). This mechanism would result in the elimination of any T lymphocyte that had a sufficient affinity for the inciting antigen. Our previous results suggest that in order for the T lymphocyte to undergo propriocidal cell death, it must be responding to IL-2 treatment, but not necessarily producing the lymphokine. We now extend these results to show that A.E7, a $T_H1$ clone that can respond to, but not produce IL-4, will undergo apoptosis by TCR stimulation if actively cycling in response to IL-4 treatment. We have also shown that normal lymph node cells driven into cell cycle by antigen receptor stimulation and either IL-2 or IL-4 treatment, undergo cell death upon subsequent TCR stimulation. Cell cycling per se is not required, because we have found that certain blocking agents do not prevent TCR-mediated apoptosis (27). Nonetheless, agents that prevent progression beyond late G1, and not those that block proliferation in S phase, were found to be capable of inhibiting apoptosis (27). Thus, we favor the hypothesis that cell cycle progression beyond late G1, stimulated by growth lymphokines such as IL-2 or IL-4, is permissive for TCR-mediated death in T lymphocytes. It is likely that cell cycle progression beyond the late G1 stage due to the transformed phenotype of T cell hybridomas and lymphomas accounts for their sensitivity to TCR-mediated apoptosis without lymphokine treatment (13–18). Our results suggest that an intrinsic property of the T lymphocyte response to a growth lymphokine such as IL-4 is the susceptibility to apoptosis upon further TCR stimulation. Moreover, this response portrays a mechanism by which an immune response to specific antigens may be naturally suppressed.

EXAMPLE II

Method for IL-4/Peptide-Mediated Apoptosis of T Lymphocytes

Figure 3:
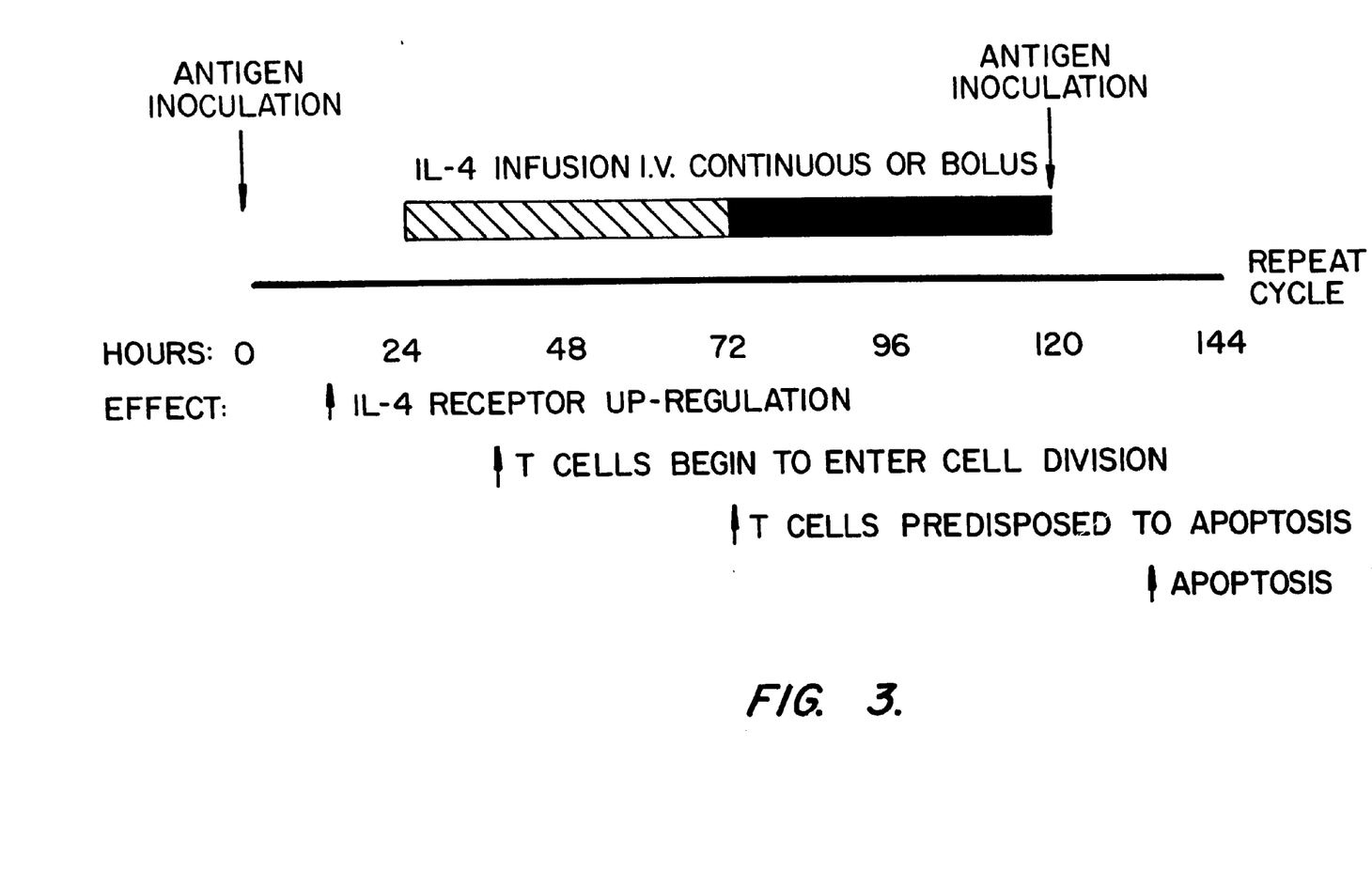
FIG. 3. Indicated is a chronological sequence of treatments (above the line) and expected outcomes (below the line). Times for antigen inoculation and IL-4 infusion are shown. Antigen may consist of protein or peptide molecules as discussed for the treatment of autoimmune diseases or red blood cells for preventing graft rejection. The hatched box indicates the earliest time frame for IL-4 treatment; the shaded box indicates optimal time for IL-4 treatment.

As shown in FIG. 3, immunization with a specific peptide or protein is carried out on day one. In the case of multiple sclerosis, for example, there is evidence that either of two immunodominant peptides from myelin basic protein (MBP) are encephalitogenic in man; MBP 84–102 (the preferred peptide), or MBP 143–168 (78,79). Either or both of these peptides, coupled to tetanus toxoid, can be given in alum adjuvant intramuscularly (IM), at a dose between about 10 to about 1000 μg. Early immunization experience using proteins or peptides has suggested that intramuscular administration is optimal (109–113). Newer data suggest that oral administration may also be effective (94).

As with any medicinal substance, or biologic, tests on any peptides and proteins used for the immunization would need to be routinely carried out over a range of doses to determine: 1) the pharmacokinetic behavior of these substances; 2) their immunogenicity; and 3) safety and identification of any untoward effects. This would constitute a Phase I clinical trial (114). Thus, the particular proteins or peptides employed in this protocol (for example, in multiple sclerosis, MBP 84–102, or MBP 143–168; in uveitis, the S Antigen; or in rheumatoid arthritis, type II collagen) would require individual routine optimization. Similar intervention could be used with preparations of allergy-inducing proteins. These could be derived from a variety of allergen protein extracts that are now used clinically, or could be generated by recombinant DNA technology for those such as hornet venom antigen 5, for which cloned DNA is available (100). Ample evidence from the development of vaccines suggests that either synthetic peptides or recombinant DNA-derived proteins are effective in eliciting an immune response in humans (109–112). These studies also provide guidance as to the range of doses effective for immunization.

Proteins:

1) Hepatitis B surface antigen, produced as a recombinant protein in yeast. Adults 2.5 to 20 μg; children 1.25 to 5 μg intramuscularly (IM). 90–96% of vaccines showed an immune response, with the best response at 10–20 μg (109). Further studies showed the efficacy of a 10 μg dose, with better results when given IM rather than subcutaneously (110). 20 μg doses in alum adjuvant given IM were found to be effective at preventing infection in clinical trials (111).

2) HIV gp 120, either natural or recombinant molecules. Doses in chimpanzees between 50–1000 μg elicit T cell responses (115).

Peptides:

1) Chorionic gonadotropin. Several studies have indicated successful immune responses against a human chorionic gonadotropin-β subunit peptide (residues 109–145) coupled to cholera or tetanus toxoid and given in doses from 50–1000 μg in alum adjuvant (112).

2) Malaria sporozoite antigen. Studies of a *Plasmodium falciparum* peptide (NANP)$_3$ coupled to tetanus toxoid showed an immune response to doses of 20–160 μg of peptide conjugate given IM, with the best response at 160 μg (113).

Immunization is then followed by a waiting period during which the antigen activates the subset of T cells bearing reactive TCRs, causing them to express IL-4 receptors and possibly IL-4. This process will only upregulate IL-4 receptors on cells that have been antigenically-stimulated (36). Based on studies of both human and mouse T cells in vitro, between about 12 to about 24 hours after antigen exposure are required to express significant increases in the numbers of IL-4 receptors, and as long as about 72 hours are required to express optimal numbers of lymphokine receptors on the majority of T cells (36). Thus, the waiting period can be as short as about 12 hours or as long as about 72 hours, becoming increasingly optimal toward the upper end of this range.

This is then followed by an infusion of high doses of IL-4. Though only very limited data exists on the clinical use of IL-4 (89–92), a great deal of information has been obtained from clinical studies using IL-2. The administration of high-doses of the related T cell growth lymphokine IL-2 to humans has been well-studied in cancer patients, and various doses have been evaluated (116–120). Data indicate that IL-2 should be given intravenously (I.V.) either as frequent bolus doses or as a continuous infusion (116–118). Doses that have been previously established range between about 300 to about 3000 units/kg/hour continuous infusion, or from $10^4$ to $10^6$ units/kg I.V. bolus (117). Units are defined by standards available from the Biological Response Modifiers Program at the National Institutes of Health, and are defined as the quantity of IL-2 or IL-4 that gave 50% maximal thymidine incorporation in the bioassay under standard conditions. Side effects of these doses included chills, fever, malaise, headache, nausea and vomiting, weight gain due to fluid retention, diarrhea, rash, and pruritus, which can all be treated with acetaminophen or indomethacin; no serious morbidity or mortality was observed. Studies of IL-4 administration to humans used human recombinant IL-4 of specific activity $1.5 \times 10^7$ units/ug, given in doses of 10–20 ug/kg body weight, three times/day. (89–91, 120,121) The side effects with IL-4 were similar to those observed with IL-2 and included weight gain due to water retention and nausea. After IL-4 treatment, the patient can be immediately reimmunized with an equivalent dose of antigen. For example, for multiple sclerosis, treatment can be carried out with about 10 to about 1000 μg of peptide MBP 84–102 coupled to tetanus toxoid and given in alum adjuvant IM. It is likely that the preferred dose would be near the upper end of this range since greater TCR stimulation produces a greater level of apoptosis (26,27). IL-4 treatment would have stimulated the T cells bearing IL-4 receptors—predominantly the disease-causing T cells—and these cells would then be re-stimulated through their TCR. These cells will then undergo apoptosis. After an immunization period of about 12 to about 72 hours, the cycle would begin again with reinfusion of IL-4. As will be described below, increased efficacy would likely result from multiple cycles of therapy. The treatment endpoints would be: i) elimination of in vitro reactivity to the antigen, which can be easily measured where possible by various mixed lymphocyte or proliferation assays using peripheral blood lymphocytes; ii) amelioration of clinical symptoms; or iii) toxicity. The treatment endpoints for allergic diseases would be: i) improvement of clinical symptoms; ii) normalization of an allergic skin test; iii) reduction in serum IgE levels; and iv) where possible to measure, reduced T cell responses to the allergenic protein.

Several features of the present therapy require further explanation. First, it is expected that T cells besides those antigenically stimulated may express high affinity IL-4 receptors. However, this should not diminish the specificity of the therapy because only those cells whose TCRs are stimulated by rechallenge with antigen will undergo apoptosis, as described supra. The effectiveness of the therapy could be variable depending on the nature of the antigen and the exact protocol employed. Extensive in vitro studies indicate that between 50–80% of the antigen-specific IL-4 stimulated T cells will undergo apoptosis when rechallenged by TCR stimulation (supra, 27). Second, the reduction in number of antigen-specific T cells determines the overall effectiveness of the therapy. Therefore, repeated cycles can substantially increase efficacy even if the level of killing in each cycle is only 50–70% (Table 3). As shown in the mouse studies, supra, the level of antigen-reactive T cells will decrease below the number of such cells prior to the first immunization with repetitive immunization. Furthermore, the expected toxicity of this protocol at moderate doses or lymphokine should be minor, and previous studies of the therapeutic use of growth lymphokines such as IL-2 or IL-4 in humans indicates that all side effects dissipate promptly following discontinuation of lymphokine treatment (89–91, 116,117). The most serious side effect, fluid retention, should be minimized by the intermittent nature of IL-4 treatment. The 2–3 day rest period between doses would allow for diuresis of the fluid built up during IL-4 administration. Finally, the repeated administration of antigen will cause production of some endogenous IL-4, which will predispose some cells to apoptosis. While it is extremely unlikely that endogenous levels can reach the very high levels of IL-4 that can be administered pharmacologically, it is possible that empirically-determined decreases in the IL-4 dose could be achieved because of endogenous IL-4 effects. The level of killing is dependent on the total level of IL-4 to which the T cell is exposed, and this will reflect a combination of endogenous and exogenous sources (supra, 26,27).

With certain antigens, the pre-disposition of cells to apoptosis may be sufficiently induced by the endogenous production of IL-4. In these cases, appropriate immunization with antigen, in the absence of exogenously administered IL-4, could produce T cell apoptosis and a protective effect. Based on the studies of the timing of susceptibility to apoptosis disclosed supra, immunizations repeated at specific intervals would be crucial for effective therapy. To effect IL-4-mediated apoptosis, immunizations would have to be repeated at about 24 to about 120 hour intervals, preferably at about 24 to about 72 hour intervals, and would have to be repeated multiple times using antigen doses at about the high end of the ranges discussed above. T cell reactivity or cell-mediated immunity for the specific antigen could then be monitored by in vitro assays to determine that T cells had undergone apoptosis. Absent the knowledge provided by the discovery disclosed herein, previous attempts to decrease immune responsiveness by repetitive immunization have not been optimal. For example, donor transfusion protocols to ameliorate graft rejection involved 3 transfusions given at 2 week intervals (122, 123). Allergy shots, i.e., desensitization therapy, are typically given initially at 4–7 day intervals, after which intervals are progressively increased in length to 2 to 4 weeks (97). Based on the present novel understanding of T cell apoptosis, the most effective immunization protocol would involve repetitive administrations of antigen at about 24 to 72 hour intervals.

TABLE 3

Theoretical number of reactive cells after fractional killing using IL-4 and T cell receptor stimulation

| Cycle | Fractional Killing | Reactive Cells Remaining |
|---|---|---|
| Start | None | 100,000 |
| 1 | 70% | 30,000 |
| 2 | 70% | 9,000 |
| 3 | 70% | 2,700 |
| 4 | 70% | 810 |
| 5 | 70% | 243 |
| 6 | 70% | 73 |

Theoretical values are based on starting with 100,000 cells and a constant killing efficiency of 70%. A reduction of over 100-fold is seen in 4 cycles and over 1000-fold in 6 cycles. At a fractional killing of 50%, a reduction of nearly 100-fold would be seen in 6 cycles. A first order kinetics is represented here because the process of apoptosis involves a single lethal hit deiivery as has been shown for apoptosis induced by antimetabolites (1–5).

EXAMPLE III

Method for Transplantation Antigen/IL-4-Mediated Apoptosis.

In medical procedures in which tissue is transferred between individuals who are genetically non-identical at their relevant histocompatibility antigen loci, herein referred to as allografting, and the transplanted tissue referred to as an allograft, the major problem encountered is rejection of the donor allograft by the host. The term "host" refers to the individual who is the recipient of the allograft, and the term "donor" refers to the individual from whom the allograft is derived. Studies of the process of graft rejection have shown that it is due to the antigen-specific activation of T lymphocytes, especially those bearing CD8 surface molecules (124). More importantly, agents that block the ability of T cells to mount an immune response in humans effectively prevent or lessen graft rejection (125). Since $CD8^+$ T cells have been shown to be susceptible to apoptosis by IL-4, supra, this phenomenon can be used as a specific means to eliminate the reactive T cells, thereby avoiding graft rejection.

Essentially the same protocol with respect to timing and IL-4 dose can be used for this therapy as was described supra for the therapy of autoimmune diseases. The major difference between this therapy and that described above is the source of antigen. Major histocompatibility complex (MHC) antigens are cell surface proteins that are tremendously polymorphic among individuals. Each individual's cells bear a genetically determined set, or haplotype, of such antigens which serve as an immunological "fingerprint" on each cell (126). This allows one's immune system, in particular those responses generated by T cells, to recognize one's own cells, and to attack only cells that do not bear the self "fingerprint" (127). There are two classes of MHC—class I antigens, found on all cells in the body; and class II antigens, found predominantly on monocytes, macrophages, B lymphocytes, dendritic cells, and activated T cells (126). It is the class I MHC antigens that are recognized by $CD8^+$ T cells that are the predominant influence in allograft rejection (124,127). Because of this complexity of MHC antigens, the simplest source is cells from the allograft donor. It has been empirically observed that transfusion of a graft recipient with donor blood suppresses graft rejection, although the mechanism of this effect is unknown, and the clinical effectiveness in many cases is modest (123). These protocols provide evidence that three transfusions of 200 ml of whole blood or packed cell equivalent from the donor is easily tolerated by the recipient with minimal side effects (122). There is evidence that the donor-transfusion in some cases elicited sensitizing antibody responses in the allograft host, and these patients were not given allografts (122). These studies possibly represent an empirical observation that pre-exposure to donor antigen suppresses the T cell response, although this is controversial (124). The present method includes administration of blood as a source of MHC antigens in doses of about 50 to about 200 ml to patients in cycle with IL-4, as indicated in FIG. 4. In the case of kidney transplants, the amount of blood could be determined by the fluid tolerance of end-stage renal disease patients. The blood can be given as either whole blood, packed cells, or washed packed cell transfusions (123). The success of treatment can be assessed by: i) a decreased requirement for general immunosuppressive medications; ii) graft survival; and iii) adequate function of the allograft. For example, the function of a transplanted kidney can be established by determining serum levels of creatinine and blood urea nitrogen (125). This can be followed by IL-4 infusion and rechallenge with blood cells as antigen as shown in FIG. 3.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

LIST OF REFERENCES CITED

1. Kerr, J. F. R, and B. V. Harmon. 1991. Definition and incidence of apoptosis: an historical perspective. In *Apoptosis:the molecular basis of cell death*, L. D. Tomei and F. O. Cope, ed. Cold Spring Harbor Laboratory Press, Plainview, N.Y., p. 5.
2. Lockshin, R. A., and Z. Zakeri. 1991. Programmed cell death and apoptosis. In *Apoptosis: the molecular basis of cell death*. L. D. Tomei and F. O. Cope, ed., Cold Spring Harbor Press, Plainview, N.Y., p. 47.
3. Cohen, J. J., R. C. Duke, V. A. Fadok, and K. S. Sellins. 1992. Apoptosis and programmed cell death in immunity. *Ann. Rev. Immunol.* 10:267.
4. Duvall, E. and A. H. Wyllie. 1986. Death and the cell. *Immunology Today* 7:115.
5. Cotter, T. G., S. V. Lennon, J. G. Glynn, and S. J. Martin. 1990. Cell death via apoptosis and its relationship to growth. Development and differentiation of both tumor and normal cells. *Anticancer Research* 10:1153.
6. von Boehmer, H. 1988. The developmental biology of T lymphocytes. *Ann. Rev. Immunol.* 6:309.
7. Marrack, P., and J. Kappler, 1987. The T cell receptor. *Science* 238:1073.
8. Smith, C. A., G. T. Williams, R. Kingston, E. J. Jenkinson, and J. J. T. Owen. 1989. *Nature* 337:181.
9. Shi, Y., R. P. Bissonnette, N. Parfrey, M. Szalay, R. T. Kubo, and D. R. Green. 1991. In vivo administration of monoclonal antibodies to the CD3 T cell receptor complex induces cell death (apoptosis) in immature thymocytes. *J. Immunol.* 146:3340.
10. McConkey, D. J., P. Hartzell, J. F. Amador-Perez, S. Orrenius, and M. Jondal. 1989. Calcium-dependent killing of immature thymocytes by stimulation via the CD3/T cell receptor complex. *J. Immunol.* 143:1801.
11. Nieto, M. A., A. Gonzalez, A. Lopez-Rivas, F. Diaz-Espada, and F. Gambon. 1990. IL-2 protects against anti-CD3-induced cell death in human medullary thymocytes. *J. Immunol.* 145:1364
12. Wyllie, A. H. 1980. Glucocorticoid-induced thymocyte apoptosis is associated with endogenous endonuclease activation. *Nature* 284:555.
13. Ashwell, J. D., R. E. Cunningham, P. D. Noguchi, and D. Hernandez. 1987. Cell growth cycle block of T cell hybridomas upon activation with antigen. *J. Exp. Med.* 165:173.
14. Mercep, M., J. A. Bluestone, P. D. Noguchi, and J. D. Ashwell. 1988. Inhibition of transformed T cell growth in vitro by monoclonal antibodies directed against distinct activating molecules. *J. Immunol.* 140:324.
15. Ucker, D. S., J. D. Ashwell, and G. Nickas. 1989, Activation-driven T cell death. 1. Requirements for de novo transcription and translation and association with genome fragmentation. *J. Immunol.* 143:3461.
16. Nickas, G. J. Meyers, L. D. Hebshi, J. D. Ashwell, D. P. Gold, B. Sydora, and D. S. Ucker. 1992. Susceptibility to cell death is a dominant phenotype: triggering of activation-driven T-cell death independent of the T-cell antigen receptor complex. *Mol. Cell. Biol.* 12:379.
17. Shi, Y., M. G. Szalay, L. Paskar, M. Boyer, B. Singh, and D. R. Green. 1990. Activation-induced cell death in T cell hybridoma is due to apoptosis. *J. Immunol.* 144:3326.
18. Odaka, C., H. Kizaki, and T. Tadakuma. 1990. T cell receptor-mediated DNA fragmentation and cell death in T cell hybridomas. *J. Immunol.* 144:2096.
19. Takahashi, S., H. T. Maecker and R. Levy. 1989. DNA fragmentation and cell death mediated by T cell antigen receptor/CD3 complex on a leukemia T cell line. *Eur. J. Immunol.* 19:1911.
20. Zacharchuk, C. M., M. Mercep, P. K. Chakraborti, S. S. Simons, Jr., and J. D. Ashwell. 1990. Programmed T lymphocyte death. Cell activation- and steroid-induced pathways are mutually antagonistic. *J. Immunol.* 145:4037.
21. Iseki, R., M. Mukai, and M. Iwata. 1991. Regulation of T lymphocyte apoptosis. Signals for the antagonism between activation- and glucocorticoid-induced death. *J. Immunol.* 147:4286.
22. Iwata, M., S. Hanaoka, and K. Sato. 1991. Rescue of thymocytes and T cell hybridomas from glucocorticoid-induced apoptosis by simulation via the T cell receptor/CD3 complex: a possible in vitro model for positive selection of the T cell repertoire. *Eur. J. Immunol.* 21:643.
23. Duke, R. C. and J. J. Cohen. 1986. IL-2 addiction: withdrawal of growth factor activates a suicide program in dependent T cells. *Lymphokine Research* 5:289.
24. Watanabe-Fukunaga, R., C. I. Brannan, N. G. Copeland, N. A. Jenkins, and S. Nagata. 1992. Lymphoproliferation disorder in mice explained by defects in Fas antigen that mediates apoptosis. *Nature* 356:314.
25. Trauth, B. C., C. Klas, A. M. J. Peters, S. Matzku, P. Moller, W. Falk, K-M. Debatin, and P. H. Krammer. 1989. Monoclonal antibody-mediated tumor regression by induction of apoptosis. *Science* 245:301.
26. Lenardo, M. J. 1991. Interleukin-2 programs mouse $\alpha\beta$ T lymphocytes for apoptosis. *Nature* 353:858.
27. Boehme, S. and Lenardo, M. J. (1992) Antigen receptor= induced apoptosis of nontransformed, mature T lymphocytes (propriocidal regulation) but not glucocorticoid-induced apoptosis, requires a distinct stage of the cell cycle (manuscript submitted).
28. Katz, P. and A. S. Fauci, Immunosuppressives and immunoadjuvants, *Immunological Diseases*, M. Somter et al., eds. (Boston: Little, Brown and Company), pp. 675–698 (1989).
29. Weiss, A., T lymphocyte activation, *Fundamental Immunology*, Second Ed., W. E. Paul, ed. (New York: Raven Press), pp. 359–384 (1989).
30. Hedrick, S. M., T lymphocyte receptors, *Fundamental Immunology*, Second Ed., W. E. Paul, ed. (New York: Raven Press), pp. 291–358 (1989).
31. Fink, P. J., M. J. Blair, L. A. Matis and S. M. Hedrick, Molecular analysis of the influences of positive selection, tolerance induction, and antigen presentation on the T cell repertoire. *J. Exp. Med.*, 172:139 (1990).
32. Tse, H. Y., R. H. Schwartz and W. E. Paul, Cell-cell interactions in the T cell proliferative response, *J. Immunol.*, 125:491–500 (1980).
33. Oksenberg, J. R., S. Stuart, A. B. Begovich, R. B. Bell, H. A. Erlich, L. Steinman and C. C. A. Bernard, Limited heterogeneity of rearranged T-cell receptor V$\alpha$-transcripts in brains of multiple sclerosis patients, *Nature* 345:344 (1990).
34. Lindahl, K. F. and D. B. Wilson, Histocompatibility antigen-activated cytotoxic T lymphocytes, *J. Exp. Med.* 145:508–522 (1977).
35. Crabtree, J., Contingent genetic regulatory events in T lymphocyte activation, *Science* 243:355–361 (1989).
36. Foxwell, B. M., Woerly, G., and Ryffel, B. (1989). Identification of interleukin-4 receptor=associated proteins and expression of high and low affinity binding on human lynphoid cells, *Eur. J. Immunol.* 19:1637–41.

37. Spits, H. et al. 1987. *J. Immunol.* 139:1142.
38. Hu-Li, J. et al. 1987. *J. Exp. Med.* 165:157.
39. Mosmann, T. R. and Coffman, R. L., 1987. Two types of mouse helper T cell clone, *Immunology Today* 89:223–227.
40. Bottomly, K. 1988. *Immunology Today* 9:268.
41. Mueller, D. L., L. Chiodetti, P. A. Bacon, and R. H. Schwartz. 1991. Clonal anergy blocks the response to IL-4, as well as the production of IL-2, in dual-producing T helper cell clones. *J. Immunol.* 146:4118.
42. Widmer, M. B. and Grabstein, K. H. 1987. *Nature:* 326:795.
43. Grabstein, K. H. et al. 1987. *J. Immunol.* 139:1148.
44. Boehme, S. and Lenardo, M. J., 1992. Manuscript in preparation.
45. Paul, W. E., The immune system: an introduction. *Fundamental Immunology*, Second Ed., W. E. Paul, ed. (New York: Raven Press) pp. 3–38 (1989).
46. Russell, J. H., White, C. L., Loh, D. Y. & Meleedy-Rey, P. *Proc. Natl. Acad. Sci.* 88, 2151–2155 (1991); and Kawabe, Y. & Ochi, A. *Nature* 349, 245–248 (1991).
47. Liu, Y. & Janeway, C. A. Jr. *J. Exp. Med.* 172, 1735–1739 (1990).
48. Webb, S., Morris, C. & Sprent, J. *Cell* 63, 1249–1256 (1990).
49. Jones, L. A., Chin, L. T., Longo, D. L. & Kruisbeek, A. M. *Science* 250, 1726–1729 (1990).
50. Rocha, B. & von Boehmer, H. *Science* 251, 1225–1228 (1991).
51. Marsh, D. G. and Norman, P. S., Antigens that cause atopic diseases, *Immunological Diseases*, Fourth Edit., M. Samter et al, Eds. Vol. II, pp. 981–1002.
52. Middleton, E. et al, Eds., *Allergy: Principles and Practice*, Third edition, (St. Louis: C. V. Mosby) (1988).
53. Johnson, D, D. A. Hafler, R. J. Fallis, M. B. Lees, R. O. Brady, R. H. Quarles and H. L. Weiner, Cell-mediated immunity to myelin-associated glycoprotein, proteolipid protein, and myelin basic protein in multiple sclerosis, *J. Neuroimmunology* 13:99–108 (1986).
54. Martin, R., M. D. Howell, D. Jaraquemada, M. Flerlage, J. Richert, S. Brostoff, E. O. Long, D. E. McFarlin and H. F. McFarland, A myelin basic protein peptide is recognized by cytotoxic T cells in the context of four HLA-DR types associated with multiple sclerosis, *J. Exp. Med.*, 173:19–24 (1991).
55. Pette, M., K. Fujita, D. Wilkinson, D. M. Altmann, J. Trowsdale, G. Giegerich, A. Hinkkanen, J. T. Epplen, L. Kappos and H. Wekerle, Myelin autoreactivity in multiple sclerosis: recognition of myelin basic protein in the context of HLA-DR2 products by T lymphocytes of multiple-sclerosis patients and healthy donors. *Proc. Natl. Acad. Sci. USA* 87:7968–7972 (1990).
56. Jaraquemada, D., R. Martin, S. Rosen-Bronson, M. Flerlage, H. F. McFarland and E. O. Long, HLA-DR2a is the dominant restriction molecule for the cytotoxic T cell response to myelin basic protein in DR2Dw2 individuals, *J. Immunol.* 145:2880–2885 (1990).
57. Martin, R., D. Jaraquemada, M. Flerlage, J. Richert, J. Whitaker, E. O. Long, D. E. McFarlin and H. F. McFarland, Fine specificity and HLA restriction of myelin basic protein-specific cytotoxic T cell lines from multiple sclerosis patients and healthy individuals, *J. Immunol.* 145:540–548 (1990).
58. Brinkman, C. J. J., W. M. Nillesen, O. R. Hommes, K. J. B. Lamers, B. E. depauw, and P. Delmotte, Cell-mediated immunity in multiple sclerosis as determined by sensitivity of different lymphocyte populations to various brain tissue antigens, *Ann. Neurology* 11:450–455 (1981).
59. Hirose, S., L. A. Donoso, T. Shinohara, A. G. Palestine, R. B. Nussenblatt and I. Gery, Lymphocyte responses to peptide M and retinal S antigen in uveitis patients, *Jpn. J. Ophthalmol.* 34:298–305 (1990).
60. de Smet, M. D., J. H. Yamamoto, M. Mochizuki, I. Gery, V. K. Singh, T. Shinohara, B. Wiggert, C. J. Chader and R. B. Nussenblatt, Cellular immune responses of patients with uveitis to retinal antigens and their fragments, *Am. J. Ophthalmol.* 110:135–142 (1990).
61. Hawrylko, E., A. Spertus, C. A. Mele, N. Oster and M. Frieri, Increased interleukin-2 production in response to human Type I collagen stimulation in systemic sclerosis patients, *Arthritis Rheum.*, 34:580–587 (1991).
62. Abdel-Nour, A. N., C. J. Elson and P. A. Dieppe, Proliferative responses of T-cell lines grown from joint fluids of patients with rheumatoid arthritis and other arthritides, *Immunol. Lett.* 12:329–33 (1986).
63. Paliard, X., S. G. West, J. A. Lafferty, J. R. Clements, J. W. Kappler, P. Marrack and B. L. Kotzin, Evidence for the effects of a superantigen in rheumatoid arthritis, *Science* 253:325–329 (1991).
64. Bottazzo, G. F., B. M. Dean, J. M. McNally, E. H. MacKay, P. G. F. Swift and D. R. Gamble, In situ characterization of autoimmune phenomena and expression of HLA molecules in the pancreas in diabetic insulitis, *New Engl. J. Med.* 313:353–360 (1985).
65. Lundkin, K. E., G. Gaudernack, E. Qvigstad, L. M. Sollid and E. Thorsby, T lymphocyte clones recognizing an HLA-DQw3.2-associated epitope involving residue 57 on the DQ beta chain, *Human Immunol.*, 22:235:46 (1988).
66. Davies, T., A. Martin, E. S. Concepcion, P. Graves, L. Cohen and A. Ben-nun, Evidence of limited variability of antigen receptors on intrathyroidal T cells in autoimmune thyroid disease, *New Eng. J. Med.* 325:238–244 (1991).
67. Volpe, R., Immunoregulation in autoimmune thyroid disease, *New Eng. J. Med.* 316:44–46 (1987).
68. Londei, M., G. F. Bottazzo and M. Feldman, Human T-cell clones from autoimmune thyroid glands: specific recognition of autologous thyroid cells, *Science* 228:85–89 (1985).
69. Dale, J. B. and E. H. Beachey, Sequence of myosin-crossreactive epitopes of streptococcal M. protein, *J. Exp. Med.*, 164:1785–1790 (1986).
70. Sobel, R. A., V. K. Tuohy and M. B. Lees, Parental MHC molecule haplotpe expression in (SJL/J×SWR)$F_1$ mice with acute experimental allergic encephalomyelitis induced with two different synthetic peptides of myeline proteolipid protein, *J. Immunol.* 146:543–549 (1991).
71. Wraith, D. C., D. E. Smilek, D. J. Mitchell, L. Steinman and H. O. McDevitt, Antigen recognition in autoimmune encephalomyelitis and the potential for peptide-mediated immunotherapy, *Cell* 59:247–255 (1989).
72. Woda, B. A., E. S. Handler, D. L. Greiner, C. Reynolds, J. P. Mordes and A. A. Rossini, T-lymphocyte requirement for diabetes in RT6-depleted diabetes-resistant BB rats, *Diabetes* 40:423–8 (1991).
73. Metroz-Dayer, M. D., A. Mouland, C. Budeau, D. Duhmel and P. Poussier, Adoptive transfer of diabetes in BB rats induced by CD4 T lymphocytes, *Diabetes* 39:928–32 (1990).
74. Seki, N., Y. Sudo, A. Yamane, S. Sugihara, Y. Takai, K. Ishihara, S. Ono, T. Hamaoka, H. Senoh and H. Fujiwara, Type II collagen-induced murine arthritis. II. Genetic control of arthritis induction is expressed on L3T4+ T cells required for humoral as well as cell-mediated immune responses to type II collagen, *Reg. Immunol.*, 2:203–212 (1989).

75. Chiocchia, G., M. C. Boissier, M. C. Ronziere, D. Herbage and C. Fournier, T cell regulation of collagen-induced arthritis in mice. I. Isolation of type II collagen-reactive T cell hybridomas with specific cytotoxic function, *J. Immunol.*, 145:519–25 (1990).

76. Caspi, R. R., F. G. Rfoberge, C. G. Mcallister, M. ElSaied, T. Kuwabara, I. Gery, E. Hanna and R. B. Nussenblatt, T cell lines mediating experimental autoimmune uveoretinitis (EAU) in the rat, *J. Immunol.*, 136:9928–933 (1986).

77. Merryman, C. F., L. Donoso, X. M. Zhang, E. HeberKatz and D. S. Gregerson, Characterization of a new potent immunopathogenic epitope in S-antigen that elicits T cells expressing V$\beta$8 and V$\alpha$2-like genes, *J. Immunol.* 146:75–80 (1991).

78. Ota, K., M. Matsui, E. L. Milford, G. A. Mackin, H. L. Weiner and D. A. Halfer, T-cell recognition of an immuno-dominant myelin basic protein epitope in multiple sclerosis, *Nature* 346:183–187 (1990).

79. Pette, M., K. Fujita, D. Wilkinson, D. M. Altmann, J. Trowsdale, G. Giegerich, A. Hinkkanen, J. T. Epplen, L. Kappas and H. Wekerle, Myelin autoreactivity in multiple sclerosis: recognition of myelin basic protein in the context of HLA-DR2 products by T lymphocytes of multiple-sclerosis patients and healthy donors, *Proc. Natl. Acad. Sci. USA* 87:7968–72 (1990).

80. Shinohara, T. V. K. Singh, M. Tsuda, K. Yamaki, T. Abe and S. Suzuki, S-Antigen: from gene to autoimmune uveitis, *Exptl. Eye Res.* 50:751–757 (1990).

81. Klimink, P. S., R. B. Claque, D. M. Grennan, P. A. Dyer, I. Smeaton and R. Harris, Autoimmunity to native type II collagen—a distinct subset of rheumatoid arthritis, *J. Rheum.*, 12:865–70 (1985).

82. Canonica, G. W., M. E. Cosulich, R. Croci, S. Ferrini, M. Bognasco, W. Dirienzo, D. Ferrini, A. Bargellesi and G. Giordano, TITLE, *Clinical Immunol. Immunopathol.* 32:132–41 (1984).

83. Kupper, T. et al. Autocrine growth of T cells independent of Interleukin-2: identification of interleukin-4 (IL4, BSF-1) as an autocrine growth factor for a cloned antigen-specific helper T cell, *J. Immunol.* 138: 4280–4287 (1987).

84. Varma, C. et a., Interleukin 7 and interleukin 4 stimulate human thymocyte growth through distinct mechanisms, *Cytokine* 2:55–59 (1990).

85. Howard, M. et al., Identification of a T cell-derived B cell growth factor distinct from interleukin 2, *J. Exp. Med.*, 155, 914–923 (1982).

86. Street, N. E. and Mosmann, T. R., *Biotherapy* 2, 347–362 (1990).

87. Solari, R. et al., Purification and characterization of recombinant human interleukin 4, *Biochemical J.* 262, 897–908 (1989).

88. Chretien, I., et al., Development of polyclonal and monoclonal antibodies for immunoassay and neutralization of interleukin-4, *J. Immunol. Methods* 117, 67–81 (1989).

89. White, M. V. et al., *Blood*, 79, 1491–1495 (1992).

90. Rubin, J. T. and Lotze, M. T., *Surgery* 111, 274–280 (1992).

91. Lotze, M. T., T cell growth factors and the treatment of patients with cancer, *Clin. Immunol. Immunopath.*, 62, 547–54 (1992).

92. Maher, D. W., Davis, I., Boyd, A. W. and Morstyn, G., Human interleukin-4: an immunomodulator with potential therapeutic applications, *Prog. Growth Factor Res.*, 3,43–56 (1991).

93. Gillis, S. "T cell derived lymphokines" in Fundamental Immunology, 2nd Edition, Ed. W. Paul, New York: Raven Press, 1989, pp. 629–630.

94. Marx, J., Testing of autoimmune therapy begins, *Science* 252:27–28 (1991).

95. El-Malik et al., *Transplantation*, 38:213–216 (1984).

96. Toda, T., Regulation of reagin formation. *Prog. Allergy*, 19:122 (1975).

97. Grammer, L. C., Principles of immunologic management of allergic diseases due to extrinsic antigens, *Allergic Diseases, Diagnosis and Management*, Third Edit., R. Patterson, Ed., pp. 358–373.

98. Marsh, D. G. and Norman, P. S., Antigens that caused atopic diseases, *Immunological Diseases*, 4th Ed., M. Somter et al., Eds. Vol. II, pp. 981–1002.

99. Elsayed, S., Titlestead, K., Apold, J. et al. A synthetic hexapeptide derived from allergen M imposing allergenic and antigenic reactivity. *Scand. J. Immunol.*, 12:171 (1980).

100. Fang, K. S. Y., Vitale, M., Fehlner, P. and King, T. P., cDNA cloning and primary structure of a white-face hornet venom allergen, antigen 5, *Proc. Natl. Acad. Sci. USA*, 85:895–899 (1988).

101. M. Wayne Flye, *Principles of Organ Transplantation*, (Philadelphia: W. B. Saunders) (1989).

102. Schwartz, R. H., A cell culture model for T lymphocyte clonal anergy, *Science*, 248:1349–1356 (1990).

103. Morahan, G., Allison, J. and Miller, J. F. A. P., Tolerance of Class I histocompatibility antigens expressed extrathymically, *Nature*, 339:622–624 (1989).

104. Beverly, B., Kong, S. -M., Lenardo, M. J. and Schwartz, R. G., Reversal of in vitro T cell cloncal energy by IL-2 stimulation, *Int'l. Immunol.*, 4, 661–671 (1992).

105. Leo, Ob., M. Foo, D. H. Sachs, L. E. Samelson, and J. A. Bluestone. 1987. Identification of a monoclonal antibody specific for a murine T3 polypeptide. *Proc. Natl. Acad. Sci. USA* 84:1374.

106. Hecht, T. T., D. L. Longo, and L. A. Matis. 1983. The relationship between immune interferon production and proliferation in antigen-specific, MHC-restricted T cell lines and clones. *J. Immunol.* 131:1049.

107. Tanaka, T., S. Z. Ben-Sasson, and W. E. Paul. 1991. IL-4 increases IL-2 production by T cells in response to accessory cell-independent stimuli. *J. Immunol.* 146:3831.

108. Seder, R., Paul, W., Davis, M., and de St. Groth, B. F., *J. Exp. Med.*, in press.

109. Zajoc, B. A., D. J. West, W. J. McAleer and E. M. Scolnick, Overview of clinical studies with Hepatitis B vaccine made by recombinant DNA, *J. Infect.* 13:(Suppl A)39–45 (1986).

110. Yamamoto, S., T. Kuroki, K. Kurai and S. Iino, Comparison of results for phase I studies with recombinant and plasma-derived hepatitis B vaccines, and controlled study comparing intramuscular and subcutneous injections of recombinant hepatitis B vaccine, *J. Infect.* 13:(Suppl A) 53–60 (1986).

111. Francis, D. P. et al., The prevention of Hepatitis B with vaccine, *Ann. Int. Med.* 97:362–366 (1982).

112. Steven, V. C. and W. R. Jones, Vacines to prevent pregnancy, *New Generation Vaccines*, G. C. Woodrow and M. M. Levine, eds. (New York: Dekker) pp. 879–900 (1990).

113. Herrington et al., Safety and immunogenicity in man of a synthetic peptide malaria vaccine against *Plasmodium Falciparium* sporozoites, *Nature*, 328:257–259 (1987).

114. Owen, J. A. Jr., Managing and conducting Phase I and Phase II clinical trials, *Drug Develoment*, Second Ed., C. E. Hamner, ed. (Boca Raton: CRC Press) pp. 159–174 (1989).

115. Putney et al., Features of HIV envelope and development of a subunit vaccine, *AIDS Vaccine Research and Clinical Trials*, S. Putney and B. Bolognesi, eds. (New York: Dekker) pp. 3–62 (1990).
116. Lotze, M. T., L. W. Frana, S. O. Sharrow, R. J. Robb and S. A. Rosenberg, In vivo administration of purified human interleukin 2. I. Half-life and immunologic effects of the Jurkat cell line-derived interleukin 2. *J. Immunol.* 134:157–166 (1985).
117. Lotze, J. T., Y. L. Malory, S. E. Ettinghausen, A. A. Rayner, S. O. Sharrow, C. A. Y. Seipp, M. C. Custer and S. A. Rosenberg, In vivo administration of purified human interleukin 2. II. Half-life, immunologic effects, and expansion of peripheral lymphoid cells in vivo with recombinant IL 2. *J. Immunol.* 135:2865–2875 (1985).
118. Donohue, J. H. and S. A. Rosenberg, The fate of interleukin-2 after in vivo administration, *J. Immunol.* 130:2203–2208 (1983).
119. Belldegrun, A., M. M. Muul and S. A Rosenberg, Interleukin 2 expanded tumor-infiltrating lymphocytes in human renal cell cancer: isolation, characterization, and antitumor activity, *Cancer Research* 48:206–214 (1988).
120. Rosenberg, S. A., M. T. Lotze, L. M. Muul, S. Leitman, A. E. Chang, S. E. Ettinghausen, Y. L. Malory, J. M. Skibber, E. Shiloni, J. T. Vetto, C. A. Seipp, C. Simpson and C. M. Reichert, Observations on the systemic administration of autologous lymphokine-activated killer cells and recombinant interleukin-2 to patients with metastatic cancer, *New Eng. J. Med.* 313:1485–1492 (1985).
121. Wong, H. et al, *J. Immunol.*, 148:2118 (1991).
122. Salvatierra, O. et al., Deliberate donor-specific blood transfusions prior to living-related renal transplantion, *Ann. Surg.* 192:543–551 (1980).
123. Opelz, G., M. R. Mickey and P. I. Terasaki, Blood transfusions and kidney transplants: remaining controversies, *Transpl. Proc.* 13:136–141 (1981).
124. Ruiz et al., Evidence that pre-transplant donor blood transfusion prevents rat renal allograft dysfunction but not the in situ autoimmune or morphologic manifestations of rejection, *Transplantation* 45:1–7 (1988); and Auchincloss, H. and D. H. Sachs, Transplantation and graft rejection, *Fundamental Immunology*, Second Ed., W. E. Paul, ed. (New York: Raven Press) pp. 889–922 (1989).
125. Cosimi, A. B., R. C. Burton, R. B. Colvin, G. Goldstein, J. T. Herrin and P. S. Russell, Treatment of acute renal allograft rejection with OKT3 monoclonal antibody, *Transplantation*, 32:535–539 (1981); and Simmons, R. L. et al, Transplantation, *Principles of Surgery*, Fifth Edit., S. I. Schwartz, G. T. Shires, and F. C. Spencer, Eds., pp. 387–458.
126. Robinson, M. A. and T. J. Kindt, Major histocompatibility antigens and genes, *Fundamental Immunology*, Second Ed., W. E. Paul, ed. (New York: Raven Press) pp. 489–540 (1989).
127. Carbone, F. J. and M. J. Bevan, Major histocompatibility complex control of T cell recognition, *Fundamental Immunology*, Second Ed., W. E. Paul, ed. (New York: Raven Press) pp. 541–5701 (1989).

What is claimed:

1. A method for eliminating a subpopulation of T cells which cause disease, the method comprising contacting a sample containing the T-cells with interleukin-4, followed by stimulation of the T cells, thereby eliminating a subpopulation of T cells which cause disease.

2. The method of claim 1, wherein the step of stimulating the T cells is carried out by contacting the sample with an antigen recognized by the T cells.

3. The method of claim 2, wherein the antigen is associated with an allergic disease.

4. A method for inhibiting a T cell immune response in a human or animal patient, the method comprising administering to the patient a first dose of antigen associated with the immune response, followed by administering to the patient interleukin-4 (IL-4) in an amount sufficient to induce proliferation of the T cells, and administering to the patient a second dose of the antigen, thereby eliminating T cells associated with the immune response.

5. The method of claim 4, wherein the IL-4 is administered about 72 hours after administering the first dose of the antigen.

6. The method of claim 4, wherein the second dose of antigen is administered simultaneously with the IL-4.

7. The method of claim 4, wherein the administration of IL-4 and the second dose of antigen is repeated after about 12 to about 72 hours.

8. A method of claim 4, wherein the T cell immune response is associated with an allergic disease.

9. The method of claim 4, wherein the antigen is a peptide.

10. The method of claim 9, wherein the peptide is administered at a dose between about 10 to about 1000 µg.

11. A method for inducing apoptosis in T cells of a human or animal patient, the method comprising:

a) administering to a human or animal patient a first dose of an antigen; and then b) administering IL-4 to the patient, thereby inducing the proliferation of said T cells; and c) administering to the patient a second dose of the antigen, thereby inducing apoptosis in T cells induced to proliferate in step b.

12. The method of claim 11, wherein the IL-4 is administered about 72 hours after administering the first dose of the antigen.

13. The method of claim 11, wherein the second dose of antigen is administered simultaneously with the IL-4.

14. The method of claim 11, wherein the administration of IL-4 and the second dose of antigen is repeated after about 12 to about 72 hours.

15. A method of claim 11, wherein the antigen is associated with an allergic disease.

16. The method of claim 11, wherein the antigen is a peptide.

17. The method of claim 16, wherein the peptide is administered at a dose between about 10 to about 1000 µg.

* * * * *